(12) United States Patent
Sadowski

(10) Patent No.: US 7,701,582 B2
(45) Date of Patent: Apr. 20, 2010

(54) METHOD AND DEVICE FOR CARRYING OUT SURFACE PLASMON RESONANCE MEASUREMENT

(75) Inventor: Janusz Sadowski, Tampere (FI)

(73) Assignee: Beanor Oy, Helsinki (FI)

( * ) Notice: Subject to any disclaimer, the term of this patent is extended or adjusted under 35 U.S.C. 154(b) by 418 days.

(21) Appl. No.: 10/579,774

(22) PCT Filed: Nov. 19, 2003

(86) PCT No.: PCT/FI03/00887

§ 371 (c)(1),
(2), (4) Date: May 21, 2007

(87) PCT Pub. No.: WO2005/050181

PCT Pub. Date: Jun. 2, 2005

(65) Prior Publication Data

US 2008/0024783 A1 Jan. 31, 2008

(51) Int. Cl.
*G01N 21/55* (2006.01)
(52) U.S. Cl. .................................. 356/445; 356/448
(58) Field of Classification Search ......... 356/445–448, 356/36–39; 359/838–839
See application file for complete search history.

(56) References Cited

U.S. PATENT DOCUMENTS

| | | | |
|---|---|---|---|
| 5,415,842 A * | 5/1995 | Maule | 422/82.05 |
| 6,628,376 B1 * | 9/2003 | Nikitin et al. | 356/38 |
| 6,738,141 B1 | 5/2004 | Thirstrup | |
| 2003/0048452 A1 * | 3/2003 | Johansen | 356/445 |
| 2003/0103208 A1 * | 6/2003 | Quinn et al. | 356/445 |

FOREIGN PATENT DOCUMENTS

| | | |
|---|---|---|
| EP | 0 341 927 A1 | 11/1989 |
| EP | 0 575 132 A1 | 12/1993 |
| GB | 2 268 800 A | 1/1994 |
| JP | 8193946 | 7/1996 |
| JP | 11271215 | 10/1999 |
| JP | 2002-148180 | 5/2002 |
| JP | 2002-536638 | 10/2002 |
| WO | WO 00/46589 | 8/2000 |
| WO | 03/034046 A1 | 4/2003 |

OTHER PUBLICATIONS

International Search Report.
Translation of Japanese Office Action dated Jul. 14, 2009 in corresponding JP Appln. No. 2005-510721 (4 pps).

* cited by examiner

*Primary Examiner*—Gregory J Toatley, Jr.
*Assistant Examiner*—Tri T Ton
(74) *Attorney, Agent, or Firm*—Buchanan Ingersoll & Rooney PC

(57) ABSTRACT

A method and a device for carrying out surface plasmon resonance measurement. A beam of electromagnetic radiation is produced by a source of electromagnetic radiation. The beam of electromagnetic radiation is directed through a prism onto a material layer in an angle of incidence, which material layer covers a planar surface of the prism. A resonance phenomenon is caused. A beam of reflected electromagnetic radiation is produced and directed by the surface to a detector for detecting the level of intensity of the beam of reflected electromagnetic radiation. The change of intensity of the beam of reflected electromagnetic radiation, caused by the surface resonance phenomenon, is measured. The beam of reflected electromagnetic radiation is reflected with a mirror to the detector.

18 Claims, 2 Drawing Sheets

METHOD AND DEVICE FOR CARRYING OUT SURFACE PLASMON RESONANCE MEASUREMENT

FIELD OF THE INVENTION

The invention relates to a method for carrying out surface plasmon resonance measurement and to a device for carrying out surface plasmon resonance measurement.

BACKGROUND OF THE INVENTION

The surface plasmon is a particular kind of electromagnetic wave which propagates along the surface of a metal (H. Raether, "Surface plasmons on smooth and rough surface and on gratings", Springer-Verlag ISBN 3-540-1760-3, Berlin, 1998). Optical excitation of the surface plasmon can be achieved if a p-polarized, collimated light beam undergoes total reflection on the surface of glass substrate (for example a prism) coated with a thin metal film (so-called Kretschmann configuration). The momentum of photons should match the surface plasmons on the opposite surface of the metal film in order to make this possible. This occurs for a certain wavelength at a critical angle of incidence of light. The phenomenon is observed as a sharp minimum in the intensity of the reflected light when the angle of the incidence (the angle between the surface of the glass substrate and the light) is varied. The angle or wavelength at which this dip occurs depends decisively on the properties of the surface layer on the top of the metal film, and therefore the phenomenon can be used to monitor changes on this surface layer caused e.g. by a specific chemical or biological reaction or by the change of concentration of some substance in the immediate vicinity of this surface.

FIG. 1 shows the principle of an arrangement for surface plasmon resonance measurement. In FIG. 1 is a beam 1 of electromagnetic radiation (e.g. a laser beam) produced by a source 2 for electromagnetic radiation (e.g. a laser) directed in an angle ($\alpha 1$; $\alpha 2$) of incidence in relation to the surface 4 through a part 3 transparent for said radiation, a semi-circular prism 3, onto a metal film 5 on the surface 4 of the prism 3. The beam 1 of electromagnetic radiation is reflected on the surface 4 of the prism 3. When the beam 1 of electromagnetic radiation is reflected on the surface 4 of the prism 3, the surface 4 produces and directs a beam 6 of reflected electromagnetic radiation at an angle ($\alpha 1$; $\alpha 2$) of reflection (which is equally large as the angle ($\alpha 1$; $\alpha 2$) of incidence in relation to the surface 4 through the prism 3 and further to a detector 7 for detecting the intensity of the beam 6 of reflected electromagnetic radiation. Surface plasmons are excited on the opposite surface of the material layer 5 by electromagnetic radiation undergoing total internal reflection (TIR) at the surface 4. Material layer 5 and possible additional layers are inside the influence zone of the evanescent field associated with the TIR.

One of the problems associated with the above arrangement is that if the prism 3 and with it the surface 4 and material layer 5 is rotated an angle $\beta$ in relation to the source 2 of electromagnetic radiation, the detector 7 for collecting the beam of reflected electromagnetic radiation should be rotated an angle 65 in relation to the surface 4, which is equal twice the angle $\beta$ of rotation of the prism 3 itself. In other words, when prism 3 is rotated an angle $\beta$, the surface 4 of the prism 3 is also rotated an angle $\beta$, which leads to that the old angle $\alpha 1$ of incidence between the beam 1 of electromagnetic radiation and the surface 4 and material layer 5 changes to a new angle $\alpha 2$ of incidence between the beam 1 of electromagnetic radiation and the surface 4 and correspondingly to that the old angle $\alpha 1$ of reflection between the beam 6 of reflected electromagnetic radiation and the surface 4 changes to a new angle $\alpha 2$ of reflection between the beam 6 of reflected electromagnetic radiation and the surface 4. This leads to that the angle (not marked with a reference numeral) between the beam 1 of electromagnetic radiation and the beam 6 of reflected electromagnetic radiation changes. In order to collect a beam 1 of electromagnetic radiation produced by the source 2 and reflected as an beam 6 of electromagnetic radiation by the surface 4, the detector 7 has therefore to be rotated an angle $\gamma$, which is twice the angle $\beta$ of the rotation of the prism itself in the arrangement shown in FIG. 1.

In the example in FIG. 1 this means that if the prism is rotated anti-clockwise 20 degrees about an axis of rotation 12 (the source of electromagnetic radiation is not rotated) the beam 1 of electromagnetic radiation from the source 4 enters the prism and strikes the material layer 5 on the surface 4 at an angle of incidence rotated 20 degrees clockwise compared to the non-rotated state and this leads to that the reflected beam exists the prism at an angle of reflection, which is rotated 40 degrees anti-clockwise compared to the non-rotated state. In the example in FIG. 1, the new angle $\alpha 2$ of incidence is 20 degrees sharper than the old angle $\alpha 1$ of incidence and correspondingly the new angle $\alpha 2$ of reflection is 20 degrees sharper than the old angle $\alpha 1$ of reflection flection. The angle between the new angle $\alpha 2$ of incidence and the new angle of $\alpha 2$ of reflection is therefore 40 degrees larger than the angle between the old angle $\alpha 1$ of incidence and the old angle of $\alpha 1$ of reflection. This is why the detector has to be rotated 40 degrees (twice as much as the angle of rotation of the prism 3) in relation to the source 1.

A solution to this problem is to have a rotating arrangement which, when the angle of the source is rotated rotates the detector 7 an angle, which is twice the angle of the rotation of the source 4. This solution is mechanically complex.

BRIEF DESCRIPTION OF THE INVENTION

It is thus an object of the present invention to provide a method and a device for carrying out surface plasmon resonance measurement so as to solve the above problem.

The objects of the invention are achieved by a method and a device for carrying out surface plasmon resonance measurement.

The preferred embodiments of the invention are disclosed in the dependent claims.

The invention is based on the idea of reflecting the beam of reflected electromagnetic radiation with a mirror to the detector, in other word to direct the beam of reflected electromagnetic radiation with a mirror to the detector.

In an arrangement, where the prism is a semi-circular prism, having a plane surface with material layer and with a longitudinal midline and the beam of electromagnetic radiation is directed perpendicularly on said longitudinal midline and where the mirror is a planar mirror arranged in plane parallel relationship with said plane surface, after the prism the beam of reflected electromagnetic radiation strikes the mirror and is reflected to the direction, which is parallel to the primary direction i.e. the direction of the beam of electromagnetic radiation produced by the source of electromagnetic radiation.

Alternatively the mirror and the surface of the prism may be nonparallel. In such an embodiment the beams of electromagnetic radiation produced by the source of electromagnetic radiation and the beams of reflected electromagnetic radiation produced (reflected) by the mirror will be nonparallel. In addition will a beam of reflected electromagnetic radiation produced (reflected) by the mirror be directed in a direction (angle), which is dependent on the angle of incidence of the beam of electromagnetic radiation produced by the source of electromagnetic radiation. This means that depending on the angle of incidence of the beam of electromagnetic radiation produced by the source of electromagnetic radiation, a beam of reflected electromagnetic radiation produced (reflected) by the mirror will be directed in certain direction (angle). When the prism is rotated together with the mirror in relation to the source of electromagnetic radiation and the detector to achieve a surface plasmon resonance phenomenon, the angle ($\alpha 1$; $\alpha 2$ in FIGS. 1 and 2) of incidence of the beam of electromagnetic radiation produced by the source of electromagnetic radiation will change with the rotation and so also the direction ($\alpha 3$; $\alpha 4$ in FIGS. 1 and 2) of the beam of reflected electromagnetic radiation produced (reflected) by the mirror. The rotation (angle $\beta$ in FIGS. 1 and 2) to achieve a surface plasmon resonance phenomenon is however normally quite small, for example 10 degrees. Therefore it is easy to set the mirror in relation to the detector in such way that the beams are directed from the surface of the prism via the mirror to the detector for all angles within angles within a given range of angles applicable in surface plasmon measurements.

The prism and the mirror can be permanently fixed together and rotated in front of a source of electromagnetic radiation (e.g. a laser) on one side and the detector on the other side. Alternatively can the source of electromagnetic radiation and the detector be permanently fixed together and rotated in relation to the prism and the mirror.

An advantage of the invention is that it enables the beam of the reflected electromagnetic radiation to be directed to the detector in a mechanically simple way. The mirror can for example be arranged in fixed relationship with the material layer on the prism.

BRIEF DESCRIPTION OF THE DRAWINGS

In the following the invention will be described in greater detail by means of preferred embodiments with reference to the attached drawings, in which.

DETAILED DESCRIPTION OF THE INVENTION

Figure 1:
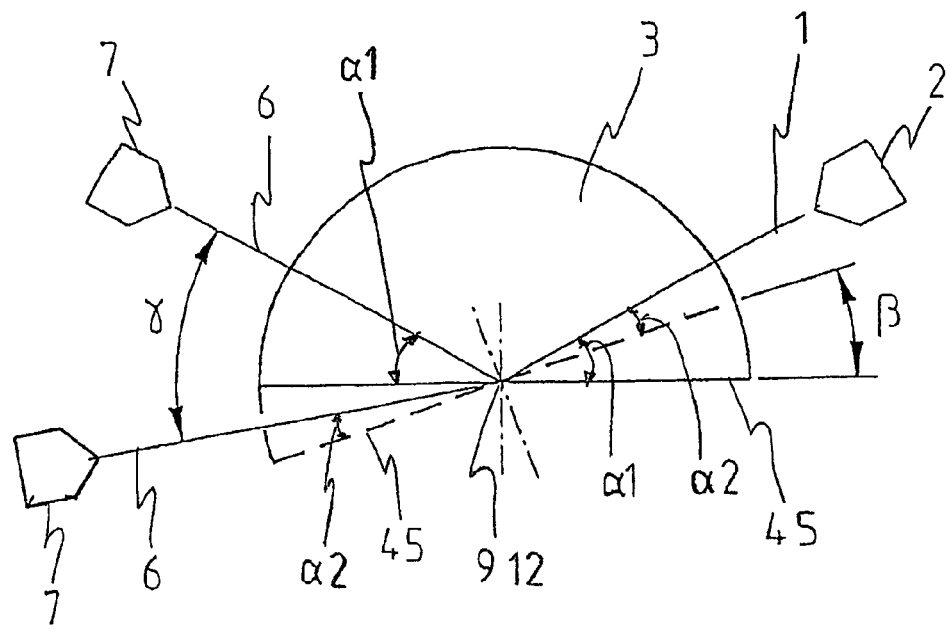
FIG. 1 shows the principle of device without a mirror.

The invention relates to a method for carrying out surface plasmon resonance measurement.

In the method a beam 1 of electromagnetic radiation is produced by a source 2 of electromagnetic radiation. The beam 1 of electromagnetic radiation is directed through a prism 3 onto a material layer 5 in an angle ($\alpha 1$; $\alpha 2$) of incidence. The material layer 5 covers at least partly a planar surface 4 of the prism 3. A surface resonance phenomenon is caused in the material layer 5. A beam 6 of reflected electromagnetic radiation is reflected by the planar surface 4 in an angle ($\alpha 1$; $\alpha 2$) of reflection through the prism 3 and further to a detector 7 for detecting the level of intensity of the beam 6 of reflected electromagnetic radiation. The change of intensity of the beam 6 of reflected electromagnetic radiation, caused by the surface resonance phenomenon, is measured. The angle ($\alpha 1$; $\alpha 2$) of incidence is equally large as the angle ($\alpha 1$; $\alpha 2$) of reflection.

In the method for carrying out surface plasmon resonance measurement the beam 6 of reflected electromagnetic radiation is reflected with a mirror 8 to the detector 7.

Figure 2:
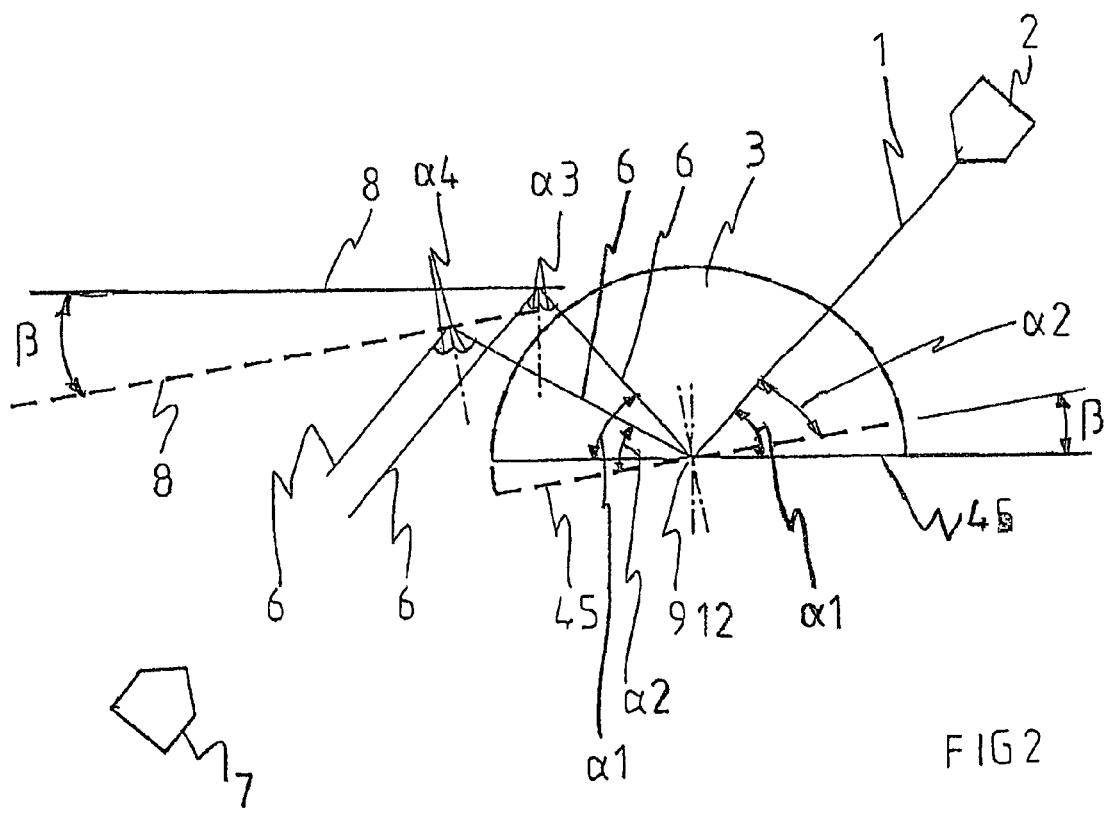
FIG. 2 shows the principle of the invention.

In FIG. 2 is a planar mirror 8 used and the planar mirror 8 is arranged plane parallel relation to the planar surface 4. This leads to that the beam 6 of reflected electromagnetic radiation strikes the planar mirror 8 in a second angle ($\alpha 3$; $\alpha 4$) of incidence, which is equally large as the angle ($\alpha 1$; $\alpha 2$) of reflection and to that the planar mirror 8 reflects the beam 6 of reflected electromagnetic radiation in a second angle ($\alpha 3$; $\alpha 4$) of reflection, which is equally large as the second angle ($\alpha 3$; $\alpha 4$) of incidence. In FIG. 2 are the beam 1 of electromagnetic radiation produced by a source 2 of electromagnetic radiation and the beam 6 of reflected electromagnetic radiation reflected by the mirror 8 therefore parallel.

Alternatively, the planar mirror 8 may be in a non-parallel, tilted relationship to the planar surface 4. In this embodiment the mirror 8 is set in relation to the planar surface 4 so that the beam 6 of reflected electromagnetic radiation is directed to the detector 7. The mirror 8 is preferably set in relation to the planar surface 4 so that beams 6 of reflected electromagnetic radiation in an angular range is directed to the detector 7.

The source 2 of electromagnetic radiation is preferably, but not necessary, a laser.

The material layer 5 is preferably a metal film, preferably but not necessary, containing Au. Other SPR-compatible materials can also be used.

The detector 7 used in the method is preferable, but hot necessary, a detector capable of detecting beams 6 of reflected electromagnetic radiation reaching the detector at a certain area, for example 10×10 mm in size. The detector 7 is preferable, but not necessary a silicon detector, fibre optics bundle or any other light collecting and detecting device.

The prism 3 in the figures is a semi-cylindrical prism 3 having a planar surface 4 having a longitudinal midline 9. The beam 1 of electromagnetic radiation is in FIGS. 1 and 2 directed onto the longitudinal midline 9.

In the method the prism 3 and the mirror 8 are preferably, but not necessary rotated together with respect to the source 2 of electromagnetic radiation and the detector 7 or vice versa about an axis of rotation 12, so that the angle ($\alpha 1$; $\alpha 2$) of incidence varies to acheive a surface plasmon resonance phenomenon.

In FIG. 2 the prism 3 is a semi-cylindrical prism 3 having a planar surface 4 having a longitudinal midline 9. The beam 1 of electromagnetic radiation is directed onto the longitudinal midline 9 and the prism 3 and the mirror 8 are together rotated about an axis of rotation 12, which also is the longitudinal midline 9 of planar surface 4 of the semi-cylindrical prism 3 so that the angle ($\alpha 1$; $\alpha 2$) of incidence varies to acheive a surface plasmon resonance phenomenon.

Figure 3:
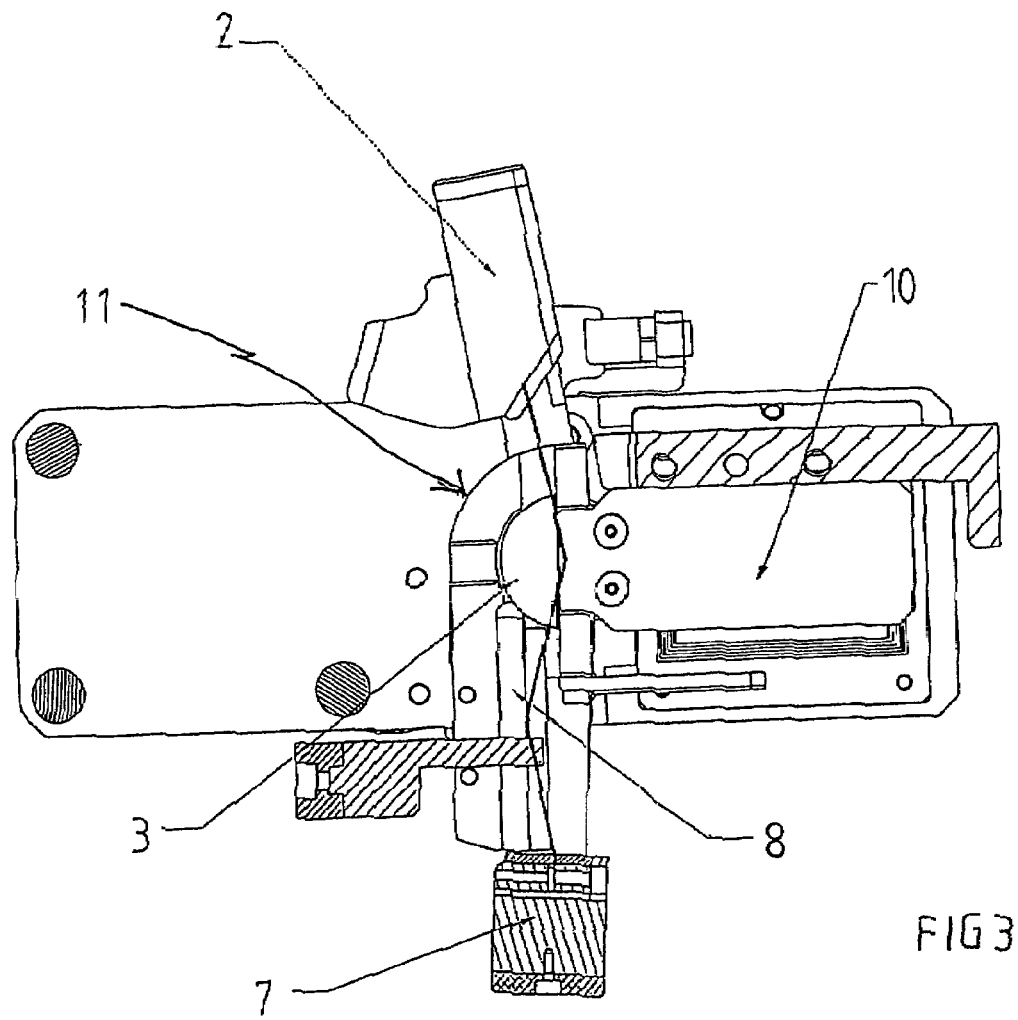
FIG. 3 shows an apparatus for detecting the presence of analytes in a sample.

In FIG. 3 the source 2 of electromagnetic radiation and the detector 7 can be rotated together with respect to the prism 3 and the mirror 8 so that the angle ($\alpha 1$; $\alpha 2$) of incidence varies to acheive a surface plasmon resonance phenomenon.

The method of the invention can for example be used as a method (or in a method) for detecting the presence of analytes 13 in a sample (not marked with a reference numeral). This can be made by arranging a sensor 11 for detecting the presence of analytes 13 in a sample in functional contact with the material layer 5.

The sensor is preferably, but not necessary the sensor presented in the application PCT/FI02/00763.

Figure 4:
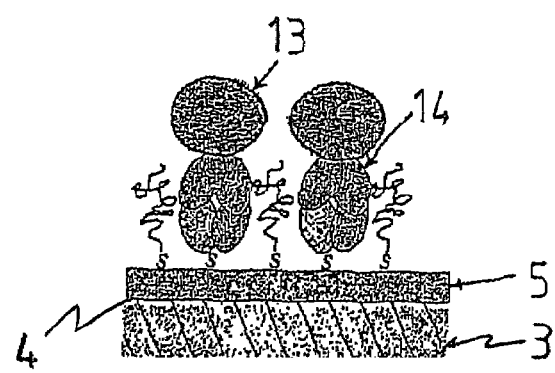
FIG. 4 shows a schematic representation of a material layer with biomolecules.

The sensor shown in FIG. 4 comprise biomolecules 14 capable of binding a specific analyte 13 to the biomolecules 14 and the sensor may so be capable of causing a change on the material layer 5 to which it is in functional contact, indicative of an increase of analyte bound to the biomolecules 14. A sample containing analytes is fed to the sensor causing analytes 13 to bound to the biomolecules 14. Because the sensor 11 is in functional contact with the material layer 5, a change in the surface plasmon resonance characteristics material layer 5 is caused, which change causes a change in the resonance phenomenon and leads to a change in the reflected electromagnetic radiation indicative of the presence of analytes in the sample fed to the sensor.

The invention also relates to a device for carrying out surface plasmon resonance measurement.

The device comprises a source 2 of electromagnetic radiation for producing and directing a beam 1 of electromagnetic radiation through a prism 3 onto a material layer 5 in such a fashion that the electromagnetic radiation meets the material layer 5 at an angle (α) of incidence enabling a surface plasmon resonance phenomenon.

The material layer 5 at least partly covers a planar surface 4 of the prism 3.

The planar surface 4 is adapted to produce a beam 6 of reflected electromagnetic radiation, which is reflected through the prism 3 and further to a detector 7 for detecting the level of intensity of the beam 6 of reflected electromagnetic radiation.

The device of the invention comprises a mirror 8 for reflecting the beam 6 of reflected electromagnetic radiation to the detector 7.

The mirror 8 shown in the figure is a planar mirror 8. The planar mirror 8 and the planar surface 4 of the prism 3 are arranged in a plane parallel relationship.

In the figures the source 2 of electromagnetic radiation is a laser and the beam 1 of electromagnetic radiation and the beam 6 of reflected electromagnetic radiation are laser beams.

The material layer 5 is preferably, but not necessary, a metal film, preferably, but not necessary, containing Au. Other SPR compatible materials are possible.

In the figures the prism 3 is a semi-cylindrical prism. Angular prisms, for example 45-degree or 60-degree prisms can also be used The detector 7 used in the method is preferable, but not necessary, a detector capable of detecting beams 6 of reflected electromagnetic radiation reaching the detector at a certain area, for example 10×10 mm in size. The detector 7 is preferable, but not necessary a silicon detector, fibre optics bundle or any other light collecting and detecting device.

The mirror 8 and the prism 3 can preferably, but not necessary, be rotated together with respect to the source 2 of electromagnetic radiation and the detector 7.

The device preferably, but not necessary, comprises a first rotating arrangement 11 for rotating the source 2 of electromagnetic radiation together with the detector 7. A such arrangement is presented in FIG. 3. The source 2 of electromagnetic radiation and the detector 7 are preferably, but not necessary, mechanically fixed to each other.

In FIG. 3 the prism 3 is a semi-cylindrical prism having a planar surface 4 having a longitudinal midline 9. The source 2 of electromagnetic radiation is arranged to direct the beam 1 of electromagnetic radiation onto the midline 9 of the planar surface 4, and the first rotating arrangement 11 is arranged to rotate the source 2 of electromagnetic radiation together with the detector 7 around the midline 9 of the planar surface 4 of the semi-cylindrical prism 3.

Alternatively or in addition can the device comprises a second rotating arrangement (not shown) for rotating the prism 3 together with the mirror 8 as is shown in FIG. 2 In this embodiment the prism 3 and the mirror 8 are preferably, but not necessary, mechanically fixed to each other. In this embodiment the second rotating arrangement can be arranged to rotate the source 2 of electromagnetic radiation together with the detector 7 around the midline 9 of the planar surface 4 of the semi-cylindrical prism 3.

The device of the invention can be used as a device (or in an apparatus) for detecting the presence of analytes in a sample. In this embodiment the device comprises a sensor for detecting the presence of analytes in a sample.

The sensor is preferably, but not necessary the sensor presented in the application PCT/FI02/00763.

In this embodiment, the sensor is in functional contact with the material layer 5. The sensor may for example comprise biomolecules capable of binding a specific analyte to the biomoleculs and the sensor is capable of causing a change in the surface plasmon resonance characteristics in the material layer 5 to which it is in functional contact, indicative of an increase of analyte bound to the biomolecules. The change in the surface plasmon resonance characteristics in the material layer 5 leads to a change in the reflected beam 6 of electromagnetic radiation.

It will be obvious to a person skilled in the art that, as the technology advances, the inventive concept can be implemented in various ways. The invention and its embodiments are not limited to the examples described above but may vary within the scope of the claims.

The invention claimed is:

1. A method for carrying out surface plasmon resonance measurement, in which method
    a beam of electromagnetic radiation is produced by a source of electromagnetic radiation,
    the beam of electromagnetic radiation is directed through a prism onto a material layer in an angle of incidence, which material layer at least partly covers a planar surface of the prism,
    a surface plasmon resonance phenomenon is caused,
    a beam of reflected electromagnetic radiation is produced and directed by the surface through the prism and further to a detector for detecting the level of intensity of the beam of reflected electromagnetic radiation,
    the change of the level of intensity of the beam of reflected electromagnetic radiation, caused by the surface resonance phenomenon, is measured, and
    the beam of reflected electromagnetic radiation being reflected with a mirror to the detector, wherein the angle of incidence is varied to cause the surface plasmon resonance phenomenon by at least one of:
    i) rotating the prism and the mirror together with respect to the source of electromagnetic radiation and the detector, and
    ii) rotating the source of electromagnetic radiation and the detector together with respect to the prism and the mirror,
    wherein the rotating of the prism and the mirror together with respect to the source of electromagnetic radiation and the detector comprises rotating the prism and the mirror each to a same first angle, so as to cause the surface plasmon resonance phenomenon, and
    wherein the rotating of the source of electromagnetic radiation and the detector together with respect to the prism and the mirror comprises rotating the source and the detector each to a same second angle, so as to cause the surface plasmon resonance phenomenon.

2. A method as claimed in claim 1, wherein a planar mirror is used as the mirror to reflect the beam of reflected electromagnetic radiation, and
   the planar mirror being arranged in plane parallel relation to the planar surface.

3. A method as claimed in claim 1, wherein the source of electromagnetic radiation is a laser.

4. A method as claimed in the claim 1, wherein the material layer comprises a metal film.

5. A method as claimed in claim 1, wherein the prism is a semi-cylindrical prism having a planar surface, which has a longitudinal midline, and
   the beam of electromagnetic radiation is directed onto the longitudinal midline.

6. A method as claimed in claim 1,
   wherein a sensor for detecting the presence of analytes in a sample is arranged in functional contact with the material layer, the sensor comprising biomolecules capable of binding a specific analyte to the biomolecules, and being configured to cause a change on the material layer to which the sensor is in functional contact, the change being indicative of an increase of analyte bound to the biomolecules, and wherein the method further comprises:
   receiving a sample containing analytes at the sensor,
   causing analytes to bind to the biomolecules,
   causing a change in the material layer, and
   causing a change in the resonance phenomenon and the reflected electromagnetic radiation indicative of the presence of analytes in the sample fed to the sensor.

7. A device for carrying out surface plasmon resonance measurement, the device comprising
   a source of electromagnetic radiation for producing and directing a beam of electromagnetic radiation through a prism onto a material layer such that the electromagnetic radiation meets the material layer at an angle of incidence enabling a surface plasmon resonance phenomenon, wherein:
   the material layer at least partly covers a planar surface of the prism,
   the planar surface is adapted to produce a beam of reflected electromagnetic radiation, which is reflected through the prism and further to a detector for detecting the level of intensity of the beam of reflected electromagnetic radiation,
   the device further comprises a mirror for reflecting the beam of reflected electromagnetic radiation to the detector; and
   a rotating arrangement for varying the angle of incidence to cause the surface plasmon resonance phenomenon by at least one of:
   i) rotating the prism and the mirror together with respect to the source of electromagnetic radiation and the detector, and
   ii) rotating the source of electromagnetic radiation and the detector together with respect to the prism and the mirror,
   wherein the rotating arrangement, when rotating the prism and the mirror together with respect to the source of electromagnetic radiation and the detector, is configured to rotate the prism and the mirror to a same first angle so as to cause the surface plasmon resonance phenomenon, and
   wherein the rotating arrangement, when rotating the source of electromagnetic radiation and the detector together with respect to the prism and the mirror, is configured to rotate the source and the detector to a same second angle so as to cause the surface plasmon resonance phenomenon.

8. A device as claimed in claim 7, wherein the mirror is a planar mirror, and
   the planar mirror and the planar surface of the prism are arranged substantially parallel to each other.

9. A device as claimed in claim 7, wherein the source of electromagnetic radiation is a laser, and
   the beam of electromagnetic radiation and the beam of reflected electromagnetic radiation are laser beams.

10. A device as claimed in claim 7, wherein the material layer comprises a metal film.

11. A device as claimed in claim 7, wherein the prism is a semi-cylindrical prism.

12. A device as claimed in claim 7, wherein the source of electromagnetic radiation and the detector are mechanically fixed to each other.

13. A device as claimed in claim 7, wherein the prism and the mirror are mechanically fixed to each other.

14. A device as claimed in claim 7, comprising a sensor for detecting the presence of analytes in a sample, the sensor being in functional contact with the material layer, the sensor comprising biomolecules capable of binding a specific analyte to the biomolecules, and being configured to cause a change on the material layer to which the sensor is in functional contact, wherein the change is indicative of an increase of analyte bound to the biomolecules.

15. A method as claimed in claim 4, wherein the metal film comprises Au.

16. A device as claimed in claim 10, wherein the metal film comprises Au.

17. A method for carrying out surface plasmon resonance measurement, the method comprising:
   producing a beam of electromagnetic radiation by a source of electromagnetic radiation,
   directing the beam of electromagnetic radiation through a prism onto a material layer in an angle of incidence, which material layer at least partly covers a planar surface of the prism, such that a resonance phenomenon is caused,
   producing and directing a beam of reflected electromagnetic radiation by the surface through the prism and to a detector configured to detect the level of intensity of the beam of reflected electromagnetic radiation,
   measuring the change of the level of intensity of the beam of reflected electromagnetic radiation, caused by the surface resonance phenomenon,
   reflecting the beam of reflected electromagnetic radiation with a mirror to the detector, and
   altering the angle of incidence to cause a surface plasmon resonance phenomenon by at least one of:
   i) rotating the prism and the mirror together with respect to the source of electromagnetic radiation and the detector, and
   ii) rotating the source of electromagnetic radiation and the detector together with respect to the prism and the mirror,
   wherein the rotating of the prism and the mirror together with respect to the source of electromagnetic radiation and the detector comprises rotating the prism and the mirror each to a same first angle, so as to cause the surface plasmon resonance phenomenon, and
   wherein the rotating of the source of electromagnetic radiation and the detector together with respect to the prism and the mirror comprises rotating the source and the detector each to a same second angle, so as to cause the surface plasmon resonance phenomenon.

18. A device for carrying out surface plasmon resonance measurement, the device comprising:
- a prism,
- a material layer at least partly covering a planar surface of the prism,
- a source of electromagnetic radiation configured to produce and direct a beam of electromagnetic radiation through the prism onto the material layer such that the electromagnetic radiation meets the material layer at an angle of incidence enabling a surface plasmon resonance phenomenon,
- a detector configured to detect the level of intensity of a beam of reflected electromagnetic radiation produced at the planar surface, the beam being reflected through the prism,
- a mirror configured to reflect the beam of reflected electromagnetic radiation to the detector
- a rotation mechanism configured to alter the angle of incidence to cause the surface plasmon resonance phenomenon by at least one of:
  i) rotating the prism and the mirror together with respect to the source of electromagnetic radiation and the detector, and
  ii) rotating the source of electromagnetic radiation and the detector together with respect to the prism and the mirror, wherein the rotation mechanism, when rotating the prism and the mirror together with respect to the source of electromagnetic radiation and the detector, is configured to rotate the prism and the mirror to a same first angle so as to cause the surface plasmon resonance phenomenon, and wherein the rotation mechanism, when rotating the source of electromagnetic radiation and the detector together with respect to the prism and the mirror, is configured to rotate the source and the detector to a same second angle so as to cause the surface plasmon resonance phenomenon.

* * * * *